(12) United States Patent
Vukovich et al.

(10) Patent No.: US 7,777,028 B2
(45) Date of Patent: Aug. 17, 2010

(54) PREPARATION OF METAL MESOPORPHYRIN COMPOUNDS

(75) Inventors: Robert A. Vukovich, Holmdel, NJ (US); Benjamin Levinson, Montgomery, NJ (US); George S. Drummond, New York, NY (US); Robert Caroselli, East Brunswick, NJ (US); Kazimierz G. Antczak, Culver, IN (US); Christopher P. Boucher, Newmarket (CA); Richard Mortimer, Toronto (CA); Daniel Levin, Toronto (CA); Keith A. Cooke, Milton (CA)

(73) Assignee: Infacare Pharmaceutical Corporation, Trevose, PA (US)

( * ) Notice: Subject to any disclaimer, the term of this patent is extended or adjusted under 35 U.S.C. 154(b) by 0 days.

(21) Appl. No.: 11/957,317

(22) Filed: Dec. 14, 2007

(65) Prior Publication Data

US 2008/0154033 A1 Jun. 26, 2008

Related U.S. Application Data

(63) Continuation of application No. 10/812,156, filed on Mar. 29, 2004, now Pat. No. 7,375,216, which is a continuation-in-part of application No. 10/453,815, filed on Jun. 3, 2003, now Pat. No. 6,818,763.

(60) Provisional application No. 60/385,498, filed on Jun. 4, 2002.

(51) Int. Cl.
C07B 47/00 (2006.01)
(52) U.S. Cl. ..................................... 540/145
(58) Field of Classification Search .................. 540/145
See application file for complete search history.

(56) References Cited

U.S. PATENT DOCUMENTS

| | | | |
|---|---|---|---|
| 4,657,902 A | 4/1987 | Kappas et al. |
| 4,684,637 A | 8/1987 | Kappas et al. |
| 4,692,440 A | 9/1987 | Kappas et al. |
| 4,782,049 A | 11/1988 | Kappas et al. |
| 4,861,876 A | 8/1989 | Kessel |
| 4,900,871 A | 2/1990 | Ellis, Jr. et al. |
| 5,192,757 A | 3/1993 | Johnson et al. |
| 5,371,199 A | 12/1994 | Therien et al. |
| 5,493,017 A | 2/1996 | Therien et al. |
| 5,817,830 A | 10/1998 | Therien et al. |
| 5,883,246 A | 3/1999 | Brückner et al. |
| 5,886,173 A | 3/1999 | Hemmi et al. |
| 5,889,181 A | 3/1999 | Kudrevich et al. |
| 5,929,064 A | 7/1999 | Goel et al. |
| 5,955,603 A | 9/1999 | Therien et al. |
| 5,973,141 A | 10/1999 | Robinson et al. |
| 5,990,363 A | 11/1999 | Wijesekera et al. |
| 6,004,530 A | 12/1999 | Sagner et al. |
| 6,114,321 A | 9/2000 | Platzek et al. |
| 6,124,452 A | 9/2000 | DiMagno |
| 6,177,561 B1 | 1/2001 | Sinn et al. |
| 6,194,566 B1 | 2/2001 | Platzek et al. |
| 6,235,895 B1 | 5/2001 | McEwan et al. |
| 6,420,553 B1 | 7/2002 | Inoue et al. |
| 6,462,192 B2 | 10/2002 | Robinson et al. |
| 6,818,763 B2 | 11/2004 | Vukovich et al. |
| 7,375,216 B2 | 5/2008 | Vukovich et al. |
| 2004/0210048 A1 | 10/2004 | Vukovich et al. |

FOREIGN PATENT DOCUMENTS

| | | |
|---|---|---|
| JP | 58-501130 A | 7/1983 |
| JP | 1-501627 A | 8/1989 |
| WO | WO-03/101999 A2 | 12/2003 |
| WO | WO-03/101999 A3 | 12/2003 |
| WO | WO-2004/045546 A2 | 6/2004 |
| WO | WO-2004/045546 A3 | 6/2004 |
| WO | WO-2005/103056 A2 | 11/2005 |
| WO | WO-2005/103056 A3 | 11/2005 |

OTHER PUBLICATIONS

Baker, E.W. et al. (Aug. 1964). "The Preparation of Mesoporphyrin IX and Etioporphrin III," *Analytical Biochemistry* 8(4):512-518.

Bauer, J. et al. (1988). "Stability-Indicating High-Performance Liquid Chromatographic Analysis of Tin Protoporphyrin and Other Free Acid Metalloporphyrins," *Journal of Chromatography* 445:429-432.

Cowan, J.A. et al. (1989). "Synthesis and Properties of Metal-Substituted Myoglobins," *Inorganic Chemistry* 28(11):2074-2078.

Delaney, J.K. et al. (Apr. 1988). "Photophysical Properties of Sn-Porphyrins: Potential Clinical Implications," *Pediatrics* 81(4):498-504.

(Continued)

*Primary Examiner*—James O. Wilson
*Assistant Examiner*—Paul V. Ward
(74) *Attorney, Agent, or Firm*—Pepper Hamilton LLP

(57) ABSTRACT

A method of preparing metal mesoporphyrin halide compounds is described. The metal mesoporphyrin halide compound may be formed by forming a novel mesoporphyrin IX intermediate compound and then converting the mesoporphyrin IX intermediate to the metal mesoporphyrin halide through metal insertion. The novel intermediate compound may be formed by a catalytic hydrogenation of hemin in acid and subsequent recovery.

14 Claims, 5 Drawing Sheets

OTHER PUBLICATIONS

Ellfolk, N. et al. (1969). "Separation of Porphyrins by Multiple Liquid-Liquid Partition," *Acta. Chem. Scand.* 23(3 part I):846-858.

International Search Report mailed Jun. 21, 2004, for PCT Patent Application No. PCT/US03/17426, filed Jun. 3, 2003, two pages.

International Search Report mailed Feb. 9, 2007, for PCT Patent Application No. PCT/US04/39240, filed Nov. 24, 2004, two pages.

Non-Final Office Action mailed Oct. 20, 2003, for U.S. Appl. No. 10/453,815, filed Jun. 3, 2003, three pages.

Non-Final Office Action mailed Jan. 30, 2007, for U.S. Appl. No. 10/812,156, filed Mar. 29, 2004, ten pages.

Notice of Allowability mailed Sep. 13, 2007, for U.S. Appl. No. 10/812,156, filed Mar. 29, 2004, two pages.

Sugihara, J.M. et al. (Nov. 1964). "Determination of Vanadyl Porphyrins by Demetalation with Hydrogen Bromide-Formic Acid," *Analytical Chemistry* 36(12):2374-2376.

Supplementary European Search Report mailed May 26, 2006, for European Patent Application No. 03736811.5, filed Jun. 3, 2003, three pages.

Taylor, J.F. (Sep. 1, 1940). "Metalloporphyrins. II. Cobalt and Manganese Mesoporphyrins in Coordination with Nitrogenous Bases," *Journal of Biological Chemistry* 135(2):569-595.

U.S. Appl. No. 11/867,559, filed Oct. 4, 2007, by Drummond et al.

Corwin, A.H. et al. (Aug.-Dec. 1946) "A Synthetic Ferroporphyrin Complex That Is Passive to Oxygen," *Journal of the American Chemical Society* 68:2473-2478.

PREPARATION OF METAL MESOPORPHYRIN COMPOUNDS

CROSS-REFERENCE TO RELATED APPLICATIONS

The present application is a continuation of U.S. patent application Ser. No. 10/812,156 filed Mar. 29, 2004 now U.S. Pat. No. 7,375,216, which is a continuation-in-part of U.S. application Ser. No. 10/453,815, filed on Jun. 3, 2003, now U.S. Pat. No. 6,818,763, which claims the benefit of U.S. Provisional Application No. 60/385,498, filed on Jun. 4, 2002, the disclosures of which are incorporated by reference herein.

BACKGROUND OF THE INVENTION

The present invention generally relates to metal mesoporphyrin halide compounds and processes for their preparation. More specifically, it relates to processes for making novel intermediate compounds, which can be converted to such mesoporphyrin halide compounds.

Tin (IV) mesoporphyrin IX dichloride or stannsoporfin is a chemical compound having the structure indicated in FIG. 1. It has been proposed for use, for example, as medicament in the treatment of various diseases including, for example, psoriasis (U.S. Pat. No. 4,782,049 to Kappas et al.) and infant jaundice (for example, in U.S. Pat. Nos. 4,684,637, 4,657,902 and 4,692,440). Stannsoporfin is also known to inhibit heme metabolism in mammals, to control the rate of tryptophan metabolism in mammals, and to increase the rate at which heme is excreted by mammals (U.S. Pat. Nos. 4,657,902 and 4,692,400 both to Kappas et al.).

Processes for obtaining stannsoporfin are known in the art. Protoporphyrin IX iron (III) chloride or hemin, of the structural formula indicated in FIG. 2, is commonly used as starting material. The hemin is generally hydrogenated to form an intermediate mesoporphyrin IX dihydrochloride, which is subsequently subjected to tin insertion, yielding stannsoporfin.

One prior method for the preparation of the intermediate mesoporphyrin IX dihydrochloride has involved catalytic hydrogenation of hemin over Pd(0) in formic acid at elevated temperature. Column chromatography of the resulting intermediate obtained by such a method yields an intermediate mesoporphyrin IX dihydrochloride product that reportedly contains about 15% of an unidentified impurity. Another preparation method for this intermediate has been typically performed at lower temperatures with heating hemin in formic acid in the presence of palladium catalyst. This process is reported to reduce the amount of the unidentified impurity; however, the reaction is difficult to drive to completion without decomposition of the intermediate product.

The above referenced methods for the preparation of the mesoporphyrin IX intermediate are used to produce only small, gram scale quantities of the product, and the product further requires subsequent isolation and purification, generally by preparative or column chromatography. Additionally, those methods in which hydrogenation is carried out at lower temperatures yield incomplete reactions, and when higher temperatures are used, degradation of the intermediate product is observed. Consequently, the crude intermediate product requires purification. Furthermore, the above referenced procedures require exceedingly high solvent volumes, thus making the process unsuitable for industrial scale up, since isolation of mesoporphyrin IX dihydrochloride or its free base is performed using a filtration process. Such filtrations and subsequent washings of the products are time-consuming, making the large-scale isolations costly and difficult. Additionally, the limited stability of mesoporphyrin IX in hydrochloric acid at the elevated temperatures required to form the dihydrochloride also complicates the industrial scale up of this process.

The insertion of various metals into porphyrin rings has been described by Fischer and Neumann (Ann. Chem. (1932), 494, 225). The reaction for the insertion of tin is performed in an acid, typically acetic acid, and further typically under reflux, using Sn (II) in the presence of an oxidant. A modified process is also described by Fuhrhop and Smith, as reported in "Porphyrins and Metalloporphyrins" p. 757, Elsevier, Amsterdam, 1975, to include sodium acetate, which buffers the solution and enhances deprotonation of the porphyrin. In most cases, the metal mesoporphyrin halide product crystallizes directly from the reaction mixture on cooling. Such crystallization may be enhanced by the addition of water or methanol.

SUMMARY OF THE INVENTION

One or more embodiments of the present invention provides a novel process for the preparation of metal mesoporphyrin halides that overcomes some of the difficulties of the processes known in the art.

It has now been discovered that, if the catalytic hydrogenation of hemin is conducted in formic acid, in two distinct states, each using different reaction conditions, a novel intermediate compound, a mesoporphyrin IX formate, is formed. This compound can be precipitated so that it can be isolated in a substantially pure, solid form. Then the substantially pure formate intermediate can be reacted to form a metal mesoporphyrin halide. This reaction of the formate intermediate can be accomplished in a single reaction with a metal to form a metal mesoporphyrin halide. Alternatively, the mesoporphyrin formate can be purified, and the purified intermediate can be used to form a metal mesoporphyrin halide. In another embodiment, the purified or unpurified mesoporphyrin formate can be converted to a mesoporphyrin IX dihydrochloride and reacted with insert metals such as tin, and obtain metal mesoporphyrin halides with a high degree of purity, capable of further purification if necessary, by simple procedures capable of being conducted on an industrial scale. Preferably, the intermediate formate is purified, converted to a mesoporphyrin dihydrochloride, and the mesoporphyrin dihydrochloride is reacted to form a metal mesoporphyrin halide.

Thus the invention provides, from one aspect, a process of preparing a mesoporphyrin IX formate, which comprises subjecting hemin to catalytic hydrogenation in formic acid, said hydrogenation being conducted in two successive steps comprising a first step of subjecting a mixture of hemin and a hydrogenation catalyst in formic acid to a first temperature and pressure for a first period of time. In one embodiment, the hydrogen pressure may be between about 30-60 psi and the temperature may be between about 85-95° C. The temperature may be held within that range for a period of about 1-3 hours.

A second step includes subjecting the mixture to a second temperature and pressure for a second period of time. In one embodiment, the second hydrogen pressure can be between about 30-60 psi and the temperatures may be between about 45-50° C. The mixture may be held to this temperature for a period of between about 3-6 hours. Mesoporphyrin IX formate is then recovered from the reaction mixture by precipitation with an organic solvent, for example an ether. Mesoporphyrin IX formate, which has the structural chemical formula indicated in FIG. 3, is a novel chemical compound.

Alternatively and preferably, the reactor may be pressurized with hydrogen gas prior to the heating step. Pressurizing the reactor with hydrogen prior to heating, in the first step of the process, reduces degradation, while exceeding the times and the temperatures set out above for the first step increases degradation. On the other hand, shorter reaction times and lower temperatures will lead to undesirable decreases in conversion, leading to low product yields. The second step as defined above completes the conversion of the hemin (Protoporphyrin IX iron (III) chloride) to mesoporphyrin IX formate.

Isolation of the intermediate product as a formate provides a readily filterable intermediate, filtering and washing of which to obtain at least a substantially high purity intermediate product (about >97%) is a simple procedure. The purity of the intermediate is important in the manufacturing of the final product, whether stannsoporfin or other metal mesoporphyrin halides, in that a higher purity intermediate produces a higher purity product. According to one or more embodiments, the mesoporphyrin IX formate intermediate can then be subjected to further purification such as reaction with metal scavengers and then converted to metal mesoporphyrin IX dihydrochloride.

Another aspect of the present invention comprises a process of converting a mesoporphyrin IX dihydrochloride to a metal mesoporphyrin halide which comprises subjecting the mesoporphyrin IX dihydrochloride to a chemical metal insertion process by reaction with a metal halide compound, under buffered, acidic reaction conditions and in the presence of an oxidant; and recovering the metal mesoporphyrin halide from the reaction mixture.

The invention provides, in another aspect, a process of purification of a metal mesoporphyrin halide, which comprises the steps of dissolving the metal mesoporphyrin halide in an aqueous basic solution to obtain a dissolved metal mesoporphyrin halide; treating said dissolved metal mesoporphyrin halide with charcoal to obtain a treated metal mesoporphyrin halide; adding said treated metal mesoporphyrin halide to a first aqueous acid solution to obtain a precipitated metal mesoporphyrin halide; triturating said precipitated metal mesoporphyrin halide in a second aqueous acid solution at elevated temperature to obtain a pharmaceutical grade pure (about or more than 97%) metal mesoporphyrin halide; and drying the pharmaceutical grade pure metal mesoporphyrin halide.

DETAILED DESCRIPTION

Figure 1:
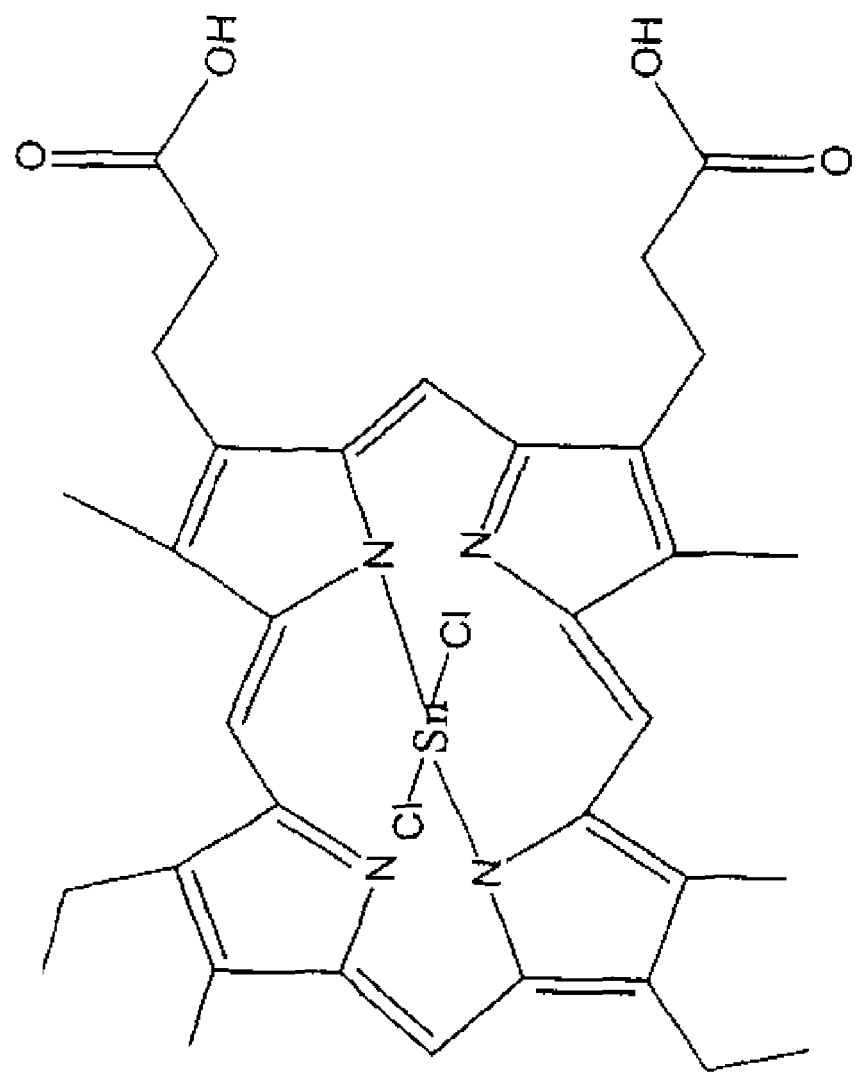
FIG. 1 illustrates the chemical structure of tin mesoporphyrin chloride (tin (IV) mesoporphyrin IX dichloride) or stannsoporfin.
Figure 2:
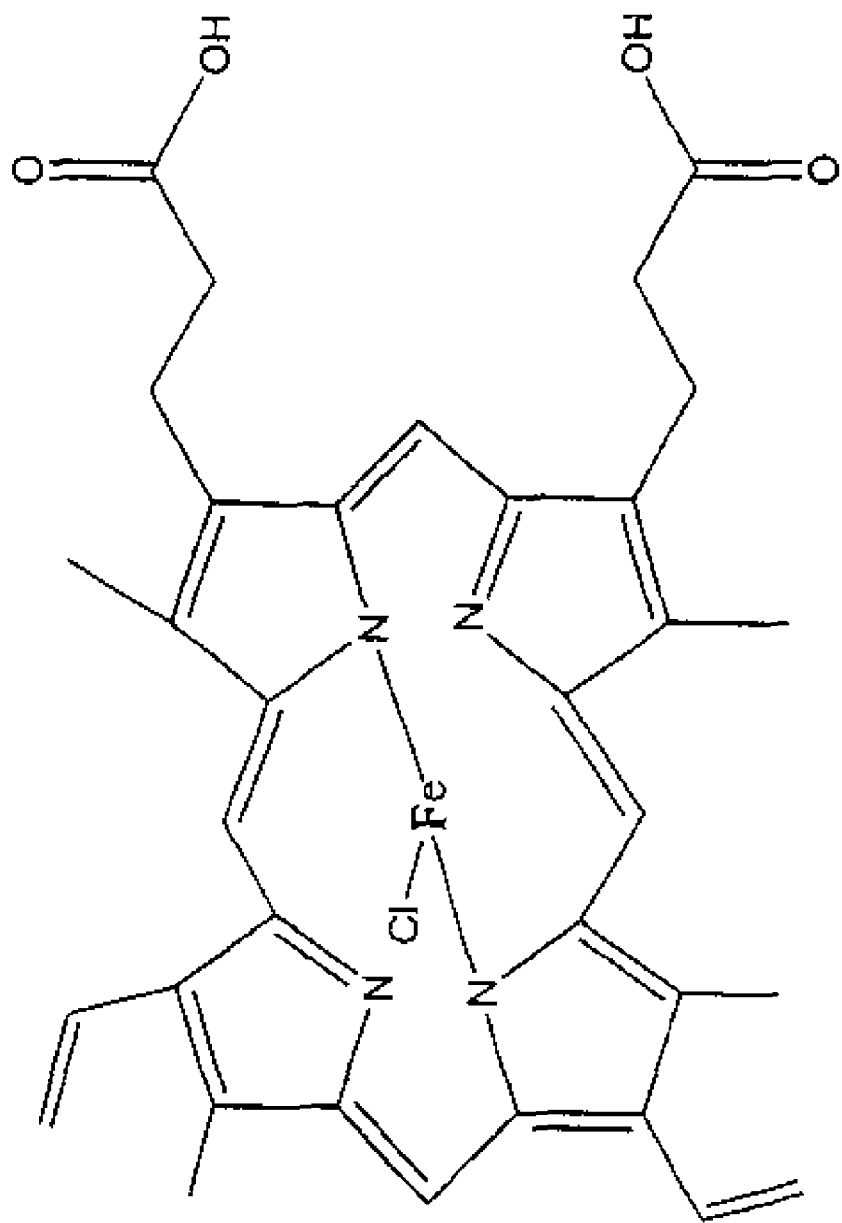
FIG. 2 illustrates the chemical structure of protoporphyrin IX iron (III) chloride or hemin.
Figure 3:
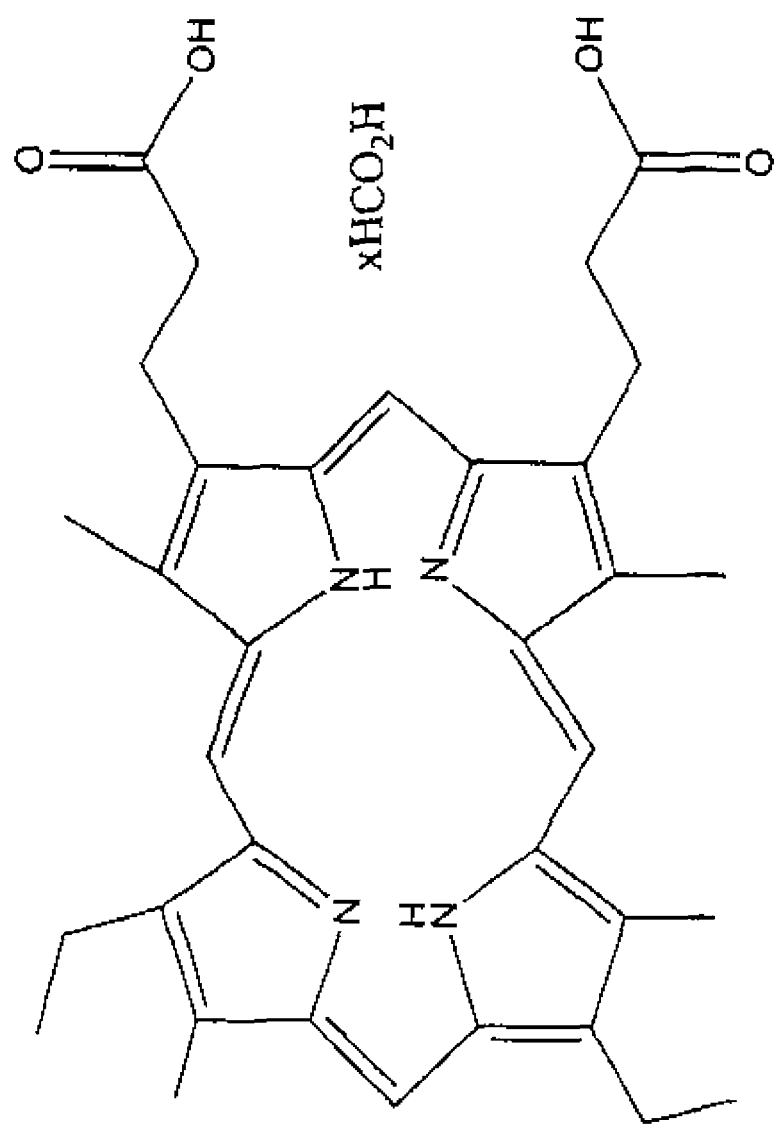
FIG. 3 illustrates the chemical structure of mesoporphyrin IX formate.
Figure 4:
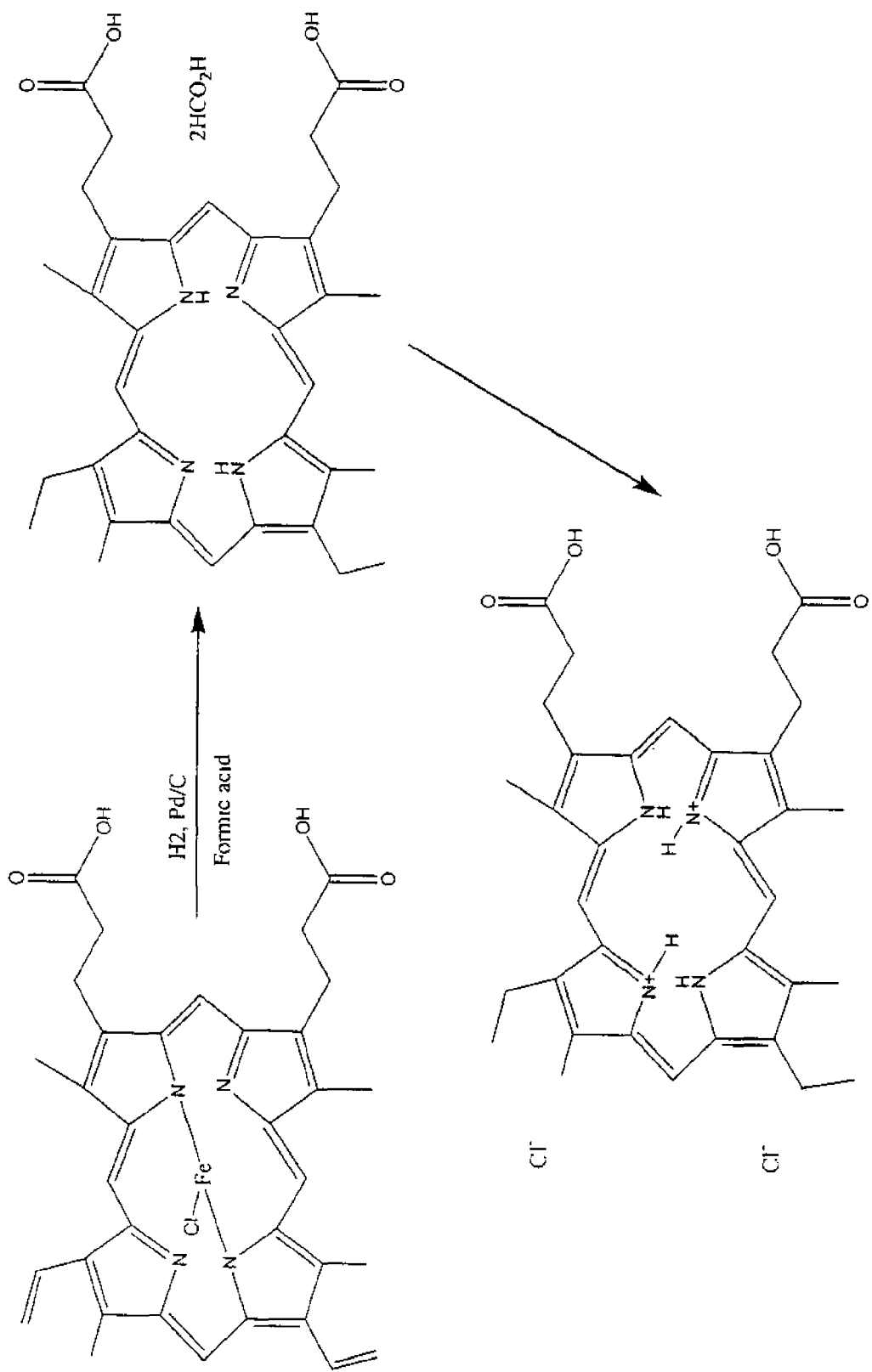
FIG. 4 illustrates the conversion of protoporphyrin IX iron (III) chloride (ferriporphyrin chloride or hemin) to mesoporphyrin IX formate to mesoporphyrin IX dihydrochloride, in accordance with one embodiment invention.

According to one embodiment of the invention, illustrated in accompanying FIG. 4, hemin is hydrogenated in formic acid, over an appropriate metal catalyst such as, for example, palladium, platinum or nickel, among others, under a hydrogen atmosphere, at elevated temperatures. Preferred embodiments of the invention involve the use of palladium on carbon as metal catalyst. According to one or more embodiments, in the first stage of hydrogenation, the temperature of hydrogenation is held at about 85-95° C. for a period of about 1-3 hours. Most preferred conditions are a temperature of about 90° C. and a time of about 1 hour.

In one or more in embodiments, in the second stage of hydrogenation, the reaction mixture is cooled to about 45-50° C. and hydrogenated for a further period of time of about 3-6 hours, in order to convert substantially all hemin (protoporphyrin IX iron (III) chloride) to mesoporphyrin IX formate. This second stage is also conducted in formic acid. The same catalyst may be used as above, so that the two stages of the process may be conducted in the same reactor. Optionally, a further charge of hydrogen may be supplied to the reactor prior to commencing the second stage. The second hydrogenation stage increases the yield of the mesoporphyrin IX formate, while reducing the amount of impurities in the final metal mesoporphyrin halide.

In contrast to previously described methods, the mesoporphyrin IX intermediate compound in the present invention is not isolated as a dihydrochloride, but rather as a formate salt.

The mesoporphyrin IX formate may be isolated from the formic acid solution by the addition of a solvent such as an ether or other organic solvent, leading directly to the mesoporphyrin IX formate intermediate, which is further subjected to drying. Ethers such as, for example, methyl tert-butyl ether, diethyl ether or di-isopropyl ether, among others, may be used. Preferred embodiments of the invention involve methyl tert-butyl ether.

The amounts of solvent used in the process according to the invention are much lower than those used in the referenced processes that involve the formation of a dihydrochloride intermediate; such smaller volumes allow for less filter time. Ratios of amount of hemin to amount of solvent of about 1:10 to about 1:20 may be used. In addition, the filtration and washings of the mesoporphyrin IX formate are rapid. After drying, the crude intermediate formate is obtained, in high yields (about 80-95%) and its purity, established by HPLC, is about or above 97%. The intermediate formate obtained in accordance with the process of the invention is of quality equal to or better than that of the intermediate mesoporphyrin IX dihydrochloride produced in the process described in the prior art, after purification by preparative chromatography.

According to one or more embodiments of the present invention, the mesoporphyrin IX formate obtained above and shown in FIG. 4 can be further purified by dissolving the formate in formic acid. A metal scavenger may be utilized to purify the formate to remove residual metal catalysts. After the scavenger is removed, the mesoporphyrin IX formate solution is mixed with hydrochloric acid to convert the formate to mesoporphyrin IX dihydrochloride. Preferred metal scavengers include, but are not limited to, silica bound scavengers such as Si-thiol, Si-thiourea, Si-triamine, and Si-triaminetetraacetic acid, which are available from Silicyle® Incorporated. The purification process is carried out for a time sufficient to remove residual metal catalyst such as palladium, which would otherwise remain as an impurity. Preferably, the purification process proceeds for more than 10 hours and less than 20 hours, for example, about 16 hours. It will be understood that the invention is not limited to any particular time, and that longer times may result in a higher purity product. The metal scavenger is then removed by charging a filtering aid such as celite and additional formic acid into the mixture. Then, the mixture is filtered to provide filtrate, which is vacuum distilled and cooled to concentrate the filtrate. The concentrated filtrate is then added to 1 N hydrochloric acid, and the resultant suspension is isolated by filtration to form mesoporphyrin IX dihydrochloride. Applicants have discovered that these additional processing steps to scavenge metal from the mesoporphyrin IX formate intermediate and form a mesoporphyrin IX dihydrochloride intermediate yields a higher purity end product (tin mesoporphyrin IX dichloride).

The insertion of metal into mesoporphyrin IX dihydrochloride to obtain metal mesoporphyrin halide is described below with specific reference to tin, to prepare stannsoporfin, a known pharmaceutical and a specific preferred embodiment of the invention. It is not intended that the scope of the invention should be limited thereto, but is generally applicable to preparation of mesoporphyrin halides, for example, but not limited to, mesoporphyrin chlorides, of other metals such as, for example, iron, zinc, chromium, manganese, copper, nickel, magnesium, cobalt, platinum, gold, silver, arsenic, antimony, cadmium, gallium, germanium and palladium, among others.

Preparation of mesoporphyrin halides of these other metals simply entails a substitution of a halide such as chloride, bromide or iodide of the chosen metal in place of stannous chloride in the process described, in substantially equivalent amounts.

Figure 5:
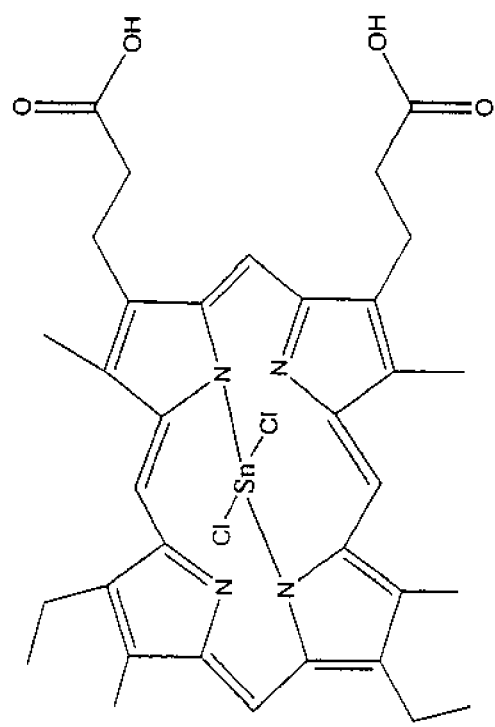
FIG. 5 illustrates the conversion of mesoporphyrin IX dihydrochloride to a tin mesoporphyrin chloride (tin (IV) mesoporphyrin IX dichloride) or stannsoporfin, in accordance with an embodiment of the invention.
Figure 5:
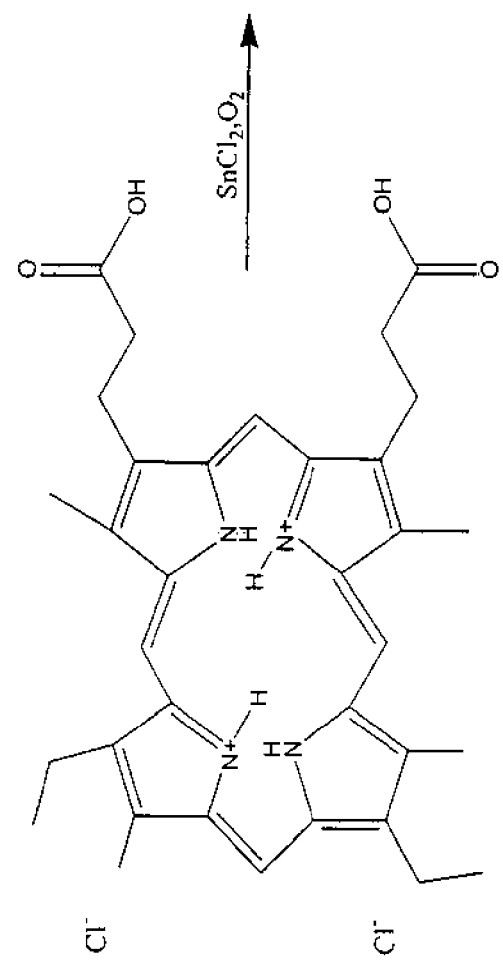

The second stage of the process according to one or more embodiments of the invention is illustrated in FIG. 5. Mesoporphyrin IX dihydrochloride is subjected to heating with a tin (II) carrier in acetic acid, in the presence of an oxidant, at reflux. Preferably, the heating is performed with aeration, for example, by an inflow of 6% oxygen mixed with nitrogen for about 24-48 hours. Air inflow could also be used to aerate during heating. Tin (II) carriers such as tin (II) halides or tin (II) acetate can be used. The reaction may also be carried out in the presence of suitable acetate counter ions include ammonium, sodium or potassium ions. Oxidants such as oxygen from air or in pure form as well as hydrogen peroxide can also be used. In one exemplary embodiment of this second stage, mesoporphyrin IX formate is subjected to heating with tin (II) chloride in acetic acid, buffered with ammonium acetate, and the reaction is conducted with aeration, at reflux. The ammonium acetate can be eliminated. Tin mesoporphyrin chloride is isolated from the reaction mixture by the addition of water, followed by filtration. Prior to drying at about 90-100° C., the cake is triturated into hot, dilute hydrochloric acid, preferably of concentration of about 0.1N-6N, at an elevated temperature, of about 90-100° C. The crude, substantially pure tin mesoporphyrin chloride (crude tin (IV) mesoporphyrin IX dichloride) is obtained with a yield of about 75-95% and a purity of about 95%, as judged by HPLC analysis.

The tin mesoporphyrin chloride so obtained may be further purified by dissolving the product in an aqueous inorganic base solution, preferably dilute ammonium hydroxide, followed by treatment with charcoal. The product is then re-precipitated by addition to an acid solution, such as acetic acid, hydrochloric acid or a mixture thereof. The above dissolving charcoal treatment and re-precipitation steps may be repeated a number of times, typically about 1-3 times in order to ensure the desired purity. Prior to drying, the cake is triturated in hot, dilute hydrochloric acid of a concentration of about 0.1N-6N, at an elevated temperature of about 90-100° C., in order to remove any residual ammonium salts. The tin mesoporphyrin chloride product (tin IV) mesoporphyrin IX dichloride or stannsoporfin) is obtained in a yield of about 50-70%, with an HPLC purity of about or greater than 97%.

The invention may also be performed to produce substantially pure or pharmaceutical quality tin mesoporphyrin chloride (tin (IV) mesoporphyrin IX dichloride or stannsoporfin) in large scale quantities, such as quantities exceeding about 0.1 kg through and including multiple kilogram amounts, by slight modifications of the above procedure, such as increased reaction or drying times as appropriate based upon the increase in scale of the starting reactants. Temperature and pressure times likewise can be modified as needed within the scope of this invention. The tin mesoporphyrin chloride product (tin (IV) mesoporphyrin IX dichloride or stannsoporfin) is obtained in the large-scale production process in a yield of about 60-90%, with an HPLC purity of about 97%.

The invention will be further described, for illustrative purposes, with reference to the following specific experimental examples.

EXAMPLE 1

Preparation of Mesoporphyrin IX Formate

A 2000 ml hydrogenation vessel was charged with 40.0 g hemin, 4.0 g 5% Pd/C (50% water by weight), and 800 ml 96% formic acid. Since hemin and mesoporphyrin IX formate as well as all reaction intermediates are reportedly light sensitive materials, care was taken throughout this entire procedure to minimize the exposure of the reaction to visible or ultraviolet light.

The vessel was flushed with a nitrogen flow for 10 minutes. With vigorous stirring, it was then pressurized to 50 psi with hydrogen for ten minutes; then depressurized, and the cycle repeated. The vessel was further pressurized to 50 psi with hydrogen and the temperature was raised to 90° C. over approximately 20 minutes.

The hydrogenation reaction was maintained at 90° C. and 45-55 psi for 1-1.5 hours. The reaction mixture was not stable for extended periods of time at 90° C. The time at this temperature was sufficient to dissolve all hemin and convert the majority of this material to the intermediate and final product, mesoporphyrin IX formate. The reaction was cooled to 50° C./50 psi over 20 minutes. This pressure and temperature were maintained for 3 hours. The reaction mixture was shown to be stable at this temperature for up to 48 hours. The reaction was cooled to 20-25° C., de-pressurized, and flushed with nitrogen.

The catalyst was removed by filtration through a bed of 20 g celite. The filter cake was rinsed with 3×50 ml formic acid and the filtrate was charged to a 2000 ml three-necked, round-bottom flask equipped with a magnetic stirbar, thermometer, and distillation bridge. The formic acid solvent was distilled off under aspirator vacuum to a residual volume of 200 ml. The distillation bridge was replaced with an addition funnel. With moderate agitation, 800 ml methyl tert-butyl ether was added drop wise over 30-60 minutes. The resultant suspension was agitated at 20-25° C. for 60 minutes prior to cooling to −20 to −25° C. for 1 to 2 hours. The suspension was filtered under reduced pressure. The filtercake was rinsed with 100 ml filtrate, followed by 2×50 ml methyl tert-butyl ether and dried under high vacuum at 40-60° C. for 24 hours. About 30-38 g of mesoporphyrin IX formate were obtained (yield of 75-95%).

EXAMPLE 2

Preparation of Substantially Pure Tin Mesoporphyrin Chloride (Tin (IV) Mesoporphyrin IX Dichloride or Stannsoporfin)

A dark 1000 ml three-necked, round-bottom flask equipped with a mechanical stirrer, condenser, bubbler, and an aeration tube was charged with 30.0 g mesoporphyrin IX formate, 34.5 g tin (II) chloride, 7.1 g ammonium acetate, and 600 ml acetic acid. The suspension was stirred at 20-25° C. for 30 minutes. Mesoporphyrin IX formate and tin mesoporphyrin as well as all reaction intermediates are reportedly light sensitive materials therefore care was taken throughout this entire procedure to minimize the exposure of the reaction to light.

The reaction was warmed to reflux, with aeration, for 3 to 4 hours. The reaction was shown to be stable at 110-115° C. for up to 48 hours. Once complete, the reaction mixture was cooled to 60-70° C. and 300 ml water was added while cooling to 20-25° C. over 60 minutes. The suspension was filtered under reduced pressure. The filtercake was rinsed with 2×60 ml water. A dark, 1000 ml, three-neck, round-bottom, flask equipped with a stir bar, thermometer, condenser, and nitrogen purge was charged with the wetcake from the above step, and 500 ml 1N HCl. The resultant suspension was warmed to 90° C. for 1 hour. The suspension was filtered under reduced pressure. The filtercake was rinsed with 2×50 ml 0.1N HCl and dried under high vacuum at 80-90° C. for 24 hours. About 25 to 28 g of crude, substantially pure (about or exceeding 95% purity) tin mesoporphyrin chloride (tin (IV) mesoporphyrin IX dichloride or stannsoporfin) was obtained for a yield of about 83-93%.

EXAMPLE 3

Further Purification of Crude, Substantially Pure Tin (IV) Mesoporphyrin Chloride (Tin (IV) Mesoporphyrin IX Dichloride or Stannsoporfin).

A darkened, 250 ml, one-neck, round-bottom flask equipped with a magnetic stirbar and nitrogen purge was charged with: 10.0 g tin (IV) mesoporphyrin chloride (tin (IV) mesoporphyrin IX dichloride), 125 ml water, and 4 ml 28% ammonium hydroxide, a sufficient amount of ammonium hydroxide to adjust the pH to 9.0-10.0. The suspension was stirred at 20-25° C. for 20-30 minutes to effect dissolution. As tin (IV) mesoporphyrin is light sensitive, dark conditions were maintained throughout this reaction sequence.

The flask was charged with 0.5 g Darco KB, and a 1.5 g Celite. The dark suspension was stirred at 20-25° C. for 1 hour. The suspension was filtered under reduced pressure through a bed of celite using a 5.5 cm Buchner funnel. The flask and filtercake were rinsed with 2×10 ml water. A dark, 1L, one-neck, round-bottom flask equipped with a magnetic stirbar, addition funnel and nitrogen purge was charged with 375 ml acetic acid, and 10 ml 37% hydrochloric acid. The filtrate from the celite filtration step was charged to the addition funnel and added dropwise to the stirring acid solution over 30-45 minutes. The suspension was stirred at 20-25° C. for 1-2 hours; then filtered under reduced pressure using a 7 cm Buchner funnel. The filtercake was rinsed with 2×10 ml water.

A darkened, 250 ml, one-neck, round-bottom flask equipped with a magnetic stirbar and nitrogen purge was charged with the tin mesoporphyrin wet cake from the above step, 125 ml water and 4 ml 28% ammonium hydroxide. The suspension was stirred at 20-25° C. for 20-30 minutes to effect dissolution and the pH adjusted to about 9.0-10.0 with additional ammonium hydroxide. The flask was charged with 0.5 g Darco KB, and 1.5 g Celite. The dark suspension was stirred at 20-25° for 1 hour. The suspension was filtered under reduced pressure through a bed of celite using a 5.5 cm Buchner funnel. The flask and filtercake were rinsed with 2×10 ml water.

A dark L one-neck, round-bottom flask equipped with a magnetic stirbar, addition funnel and nitrogen purge was charged with 375 ml acetic acid, and 10 ml 37% hydrochloric acid. Once the addition was complete, the pH was adjusted to about less than or equal to 1 by the addition of 37% hydrochloric acid. The filtrate from the above celite filtration step was charged to the addition funnel and added dropwise to the stirring acid solution over 30-45 minutes. Once the addition was complete, the pH was adjusted to about less than or equal to 1 by the addition of hydrochloric acid. The suspension was stirred at 20-25° C. for 1-2 hours; then filtered under reduced pressure using a 7 cm Buchner funnel. The filtercake was rinsed with 2×10 ml water.

A darkened, 250 ml, one-neck, round-bottom flask equipped with a magnetic stirbar and nitrogen purge was charged with tin mesoporphyrin wet cake from the above step, 125 ml water, and 4 ml 27% ammonium hydroxide. The suspension was stirred at 20-25° C. for 20-30 minutes to effect dissolution. The pH was adjusted to about 9.0-10.0 with additional ammonium hydroxide. The flask was charged with 0.5 g Darco KB, and 1.5 g Celite. The dark suspension was stirred at 20-25° C. for 1 hour. The suspension was filtered under reduced pressure through a bed of celite using a 5.5 cm Buchner funnel. The flask and filtercake were rinsed with 2×10 ml water.

A dark 1 L one-neck, round-bottom flask equipped with a magnetic stirbar, addition funnel and nitrogen purge was charged with 375 ml acetic acid, and 10 ml 37% hydrochloric acid. The filtrate from the celite filtration step was charged to the addition funnel and added dropwise to the stirring acid solution over 30-45 minutes. Once the addition was complete, the pH was adjusted to about less than or equal to 1 by the addition of hydrochloric acid. The suspension was stirred at 20-25° C. for 1-2 hours; then filtered under reduced pressure using a 7 cm Buchner funnel. The filtercake was rinsed with 2×10 ml water.

A dark 500 ml, one-neck, round-bottom flask equipped with a stirbar, condenser, and nitrogen purge was charged with tin mesoporphyrin wetcake from the above step and 200 ml IN HCl. The suspension, which ideally has a red color, was warmed to about 85-90° C. for 1-2 hours. The reaction was cooled to 20-25° C. and the suspension was filtered under reduced pressure using a 7 cm Buchner funnel. The filter cake was rinsed with 2×20 ml 0.1N HCl and dried at 85-90° C. for 24-48 hours. About 5 to 7 g of pharmaceutical grade pure tin mesoporphyrin chloride (tin (IV) mesoporphyrin IX dichloride) were obtained, for about a 50-70% yield, with a purity greater than or equal to 99%, as judged by HPLC analysis.

EXAMPLE 4

Representative Large Scale Production of Tin Mesoporphyrin IX Chloride (Tin (IV) Mesoporphyrin IX Dichloride or Stannsoporfin)

Step 1

A 200 L reaction vessel, which has been pressure tested and inerted with nitrogen, is charged with 0.6 kg of 5% palladium on carbon (50% water by weight). Without agitation, the vessel is charged with 6.0 kg hemin and 161.0 kg formic acid, while minimizing the exposure of the ingredients throughout this reaction to visible or ultraviolet light. The vessel is pressurized with hydrogen to 30-35 psi at 20-25° C. The reaction mixture is agitated vigorously for a minimum of 30 minutes and warmed to 85-90° C. With vigorous agitation, the reaction temperature is maintained at 85-90° C. with a hydrogen pressure of 45-55 psi for a period of 60-75 minutes. The reaction is then cooled to 45-50° C. while maintaining pressure and hydrogenation is continued for a further 6 hours. The reaction is cooled to 20-25° C. The reactor is depressurized and inerted (flushed) with nitrogen. The reactor is charged with a dispersion agent, such as 3.0 kg hyflo supercel, suspended in 36 kg formic acid. The reaction mixture is then filtered to remove the catalyst.

The filtercake is rinsed with 2×61 kg formic acid. 170 L of the filtrate is transferred to a 200 L reaction vessel and cooled to 10-15° C. The reaction mixture is distilled under a reduced pressure of 20-60 mmHg, with a maximum reactor temperature of 50° C., to a residual volume of 25-35 L. The remainder of the filtrate is transferred into the reactor and cooled to 10-15° C. The reaction mixture is distilled under a reduced pressure of 20-60 mmHg, with a maximum reactor temperature of 50° C., to a residual volume of 25-35 L. The temperature of the reactor is cooled to 20-25° C. The reaction vessel is charged with 89.1 kg methyl tert-butyl ether over a minimum of 1 hour. Upon completion of the addition, the reaction is agitated at 20-25° C. for a minimum of 2 hours. The reaction mixture is cooled to −20 to −25° C. over a minimum of 1 hour. The reaction is agitated at −20 to −25° C. for a period of 4 hours. The suspension is filtered through a cotton terylene cloth at −20 to −25° C. The filtercake is rinsed with 2×6 kg methyl tert-butyl ether. The product is dried under vacuum with a maximum oven temperature of 55° C. until it passes drying specifications. Once dry, the product (mesoporphyrin IX formate) is packaged. The theoretical yield for this reaction is 6.1 kg. Typically, the product is isolated with a yield of 4.6-5.8 kg (75-95%).

Step 2

An inerted reaction vessel is charged with 5.3 kg tin (II) chloride, 1.1 kg ammonium acetate, and 45.3 kg acetic acid. The suspension is moderately agitated at 20-25° C. for a minimum period of 2 hours. An inerted 200 L reaction vessel is charged with 4.6 kg mesoporphyrin IX formate from step 1, and 45.0 kg acetic acid. The mesoporphyrin suspension is warmed to 45-55° C. with moderate agitation for a period of 2 hours. With moderate agitation, under nitrogen, the tin chloride suspension is transferred into the mesoporphyrin suspension while maintaining a temperature of 45-55° C. in the vessel. The transfer lines are rinsed with 5.9 kg acetic acid. With vigorous agitation, nitrogen and air are bubbled into the reaction at such a rate so as to maintain an oxygen level less than 2% within the reactor. This aeration is maintained throughout the reaction. With vigorous agitation, the reaction mixture is warmed to reflux (ca. 110° C.) for a minimum period of 3 hours.

The reaction is cooled to 60-70° C. and 45.8 kg purified (de-ionized) water is added over a minimum of 30 minutes. With moderate agitation, the reaction temperature is cooled to 20-25° C. over a minimum of 1 hour. The reaction mixture is agitated at 20-25° C. for a minimum of 1 hour. The product is filtered through a cotton terylene cloth and the filtercake rinsed with 2×9 kg purified water. The wet filtercake is transferred to a 200 L reaction vessel followed by 30.1 kg purified water, 4.6 kg 31% hydrochloric acid. The transfer lines are rinsed with 5 kg purified water. With moderate agitation, the suspension is warmed to 85-90° C. for a period of 1-3 hours. The reaction mixture is cooled to 20-25° C. and 31.0 kg acetone is added over a minimum period of 30 minutes. The suspension is agitated at 20-25° C. for a minimum of 1 hour.

The product is filtered through a cotton terylene cloth and the filtercake rinsed with 2×6 kg acetone. The product is dried under a stream of nitrogen on the filter until it passes drying specifications. Once dry, the crude product (substantially pure (about or more than 95%) tin (IV) mesoporphyrin IX dichloride) is packaged. The theoretical yield for this reaction is 5.3 kg. Typically, the crude, substantially pure tin mesoporphyrin product is isolated with a yield of 4.0-4.8 kg (75-90% yield).

Step 3

An inerted 200 L reactor is charged with 1.8 kg crude, substantially pure tin mesoporphyrin, formed via Steps 1 and 2, and 31 kg WFI (water for injection) with moderate agitation at 20-25° C. The reactor is charged with 2.4 kg 28% ammonium hydroxide. The resultant solution is agitated at 20-25° C. for 30 minutes, prior to testing pH to ensure that it is greater than 9. If not, additional ammonium hydroxide is added in small portions until this pH level is achieved. To the resultant solution is charged 0.1 kg Darco KB activated carbon and 0.2 kg hyflo supercel suspended in 2.3 kg purified water. With moderate agitation, the suspension is agitated at 20-25° C. for a minimum of 30 minutes. The suspension is filtered through a sparkler filter to remove solids, leaving a filtrate. The filter cake is rinsed with 13 kg purified water. An inerted 200 L reactor is charged with 69.3 kg acetic acid and 3.1 kg 31% hydrochloric acid. With moderate agitation, under nitrogen while maintaining a temperature of 20-25° C. the filtrate is added to the acetic acid HCl solution over a minimum of 45 minutes. The resultant suspension is agitated for 15 minutes at 20-25° C. prior to testing the pH level to ensure that the final pH is about less than or equal to 1. If not, additional hydrochloric acid is added in small portions until this pH level is achieved. The suspension is then agitated at 20-25 C for a minimum of 1 hour. The product is filtered through a cotton terylene cloth and the filter cake is rinsed with 2×5 kg purified water.

With moderate agitation, at 20-25° C., an inerted 200 L reactor is charged with 31 kg purified water and 2.4 kg 28% ammonium hydroxide. The solution is then recirculated through the filtercake in order to completely dissolve all wetcake. The resultant solution is agitated at 20-25° C. for 30 minutes, prior to testing pH to ensure that it is greater than 9. If not, additional ammonium hydroxide is added in small portions until this level is achieved. To the resultant solution is charged 0.1 kg Darco KB activated carbon and 0.2 kg hyflo supercel suspended in 2.3 kg purified water. With moderate agitation, the suspension is agitated at 20-25° C. for a minimum of 30 minutes. The suspension is filtered through a sparkler filter to remove solids, leaving a filtrate. The filter cake is rinsed with 13 kg purified water. An inerted 200 L reactor is charged with 69.3 kg acetic acid and 3.1 kg 31% hydrochloric acid. With moderate agitation, under nitrogen while maintaining a temperature of 20-25° C. the filtrate is added to the acetic acid HCl solution over a minimum of 45 minutes. The resultant suspension is agitated for 15 minutes at 20-25° C. prior to testing the pH level to ensure that the final pH is about less than or equal to 1. If not, additional hydrochloric acid is added in small portions until this pH level is achieved. The suspension is then agitated at 20-25° C. for a minimum of 1 hour. The product is filtered through a cotton terylene cloth and the filter cake is rinsed with 2×5 kg purified water.

With moderate agitation, at 20-25° C., an inerted 200 L reactor is charged with 31 kg purified water and 2.4 kg 28% ammonium hydroxide. The solution is then recirculated through the filtercake in order to completely dissolve all wetcake. The resultant solution is agitated at 20-25° C. for 30 minutes, prior to testing pH to ensure that it is greater than 9. If not, additional ammonium hydroxide is added in small portions until this level is achieved. To the resultant solution is charged 0.1 kg Darco KB activated carbon and 0.2 kg hyflo supercel suspended in 2.3 kg purified water. With moderate agitation, the suspension is agitated at 20-25° C. for a minimum of 30 minutes. The suspension is filtered through a sparkler filter to remove solids, leaving a filtrate. The filter cake is rinsed with 13 kg purified water. An inerted 200 L reactor is charged with 69.3 kg acetic acid and 3.1 kg 31% hydrochloric acid. With moderate agitation, under nitrogen while maintaining a temperature of 20-25° C. the filtrate is added to the acetic acid/HCl solution over a minimum of 45 minutes. The resultant suspension is agitated for 15 minutes at 20-25° C. prior to testing the pH level to ensure that the final pH is about less than or equal to 1. If not, additional hydrochloric acid is added in small portions until this pH level is achieved. The suspension is then agitated at 20-25° C. for a minimum of 1 hour.

The resulting product is filtered through a cotton terylene cloth and the filter cake is rinsed with 2×5 kg purified water and 2×4 kg acetone. The filter cake product is dried under vacuum with a maximum oven temperature of 100° C. until it passes drying specifications. Once dry, the pharmaceutical grade pure product (tin (IV) mesoporphyrin IX dichloride or stannsoporfin) is packaged and is of pharmaceutical grade quality, as verified by analytical HPLC technique. The theoretical yield for this reaction is 1.8 kg. Typically, the final product is isolated with a yield of 1.1-1.6 kg (60-90%) and is pharmaceutical grade pure (at least about or exceeding 97%).

EXAMPLE 5

Representative Large Scale Production of Tin Mesoporphyrin IX Chloride (Tin (IV) Mesoporphyrin IX Dichloride or Stannsoporfin)

Step 1

Without agitation, a 200 L reaction vessel which has been pressure tested and inerted with nitrogen is charged with 0.6 kg of 5% palladium on carbon (50% water by weight), 6.0 kg hemin and 161.0 kg formic acid, while minimizing the exposure of the ingredients throughout this reaction to visible or ultraviolet light. The vessel is pressurized with hydrogen to 30-35 psi at 20-25° C. The reaction mixture is agitated vigorously for a minimum of 30 minutes and warmed to 85-90° C. With vigorous agitation, the reaction temperature is maintained at 85-90° C. with a hydrogen pressure of 55-65 psi for a period of 60-90 minutes. The reaction is then cooled to 45-50° C. while maintaining pressure and hydrogenation is continued for a further 24-48 hours. The reaction is cooled to 20-25° C. The reactor is depressurized and inerted (flushed) with nitrogen. The reactor is charged with a dispersion agent, such as 3.0 kg hyflo supercel and 2.3 kg of DARCO KB, suspended in 36 kg formic acid. The reaction mixture is then filtered to remove the catalyst.

The filtercake is rinsed with 122 kg formic acid. 170 L of the filtrate is transferred to a 200 L reaction vessel and cooled to 10-15° C. The reaction mixture is distilled under a reduced pressure of 20-60 mmHg, with a maximum batch temperature of 50° C., to a residual volume of 25-35 L. The remainder of the filtrate is transferred into the reactor and cooled to 10-15° C. The reaction mixture is distilled under a reduced pressure of 20-60 mmHg, with a maximum batch temperature of 50° C., to a residual volume of 25-35 L. The temperature of the reactor is cooled to 20-25° C. The reaction vessel is charged with 89.0 kg methyl tert-butyl ether over a minimum of 1 hour. Upon completion of the addition, the reaction is agitated at 20-25° C. for a minimum of 2 hours. The reaction mixture is cooled to −20 to −25° C. over a minimum of 1 hour. The reaction is agitated at −20 to −25° C. for a period of 4 hours. The suspension is filtered through a cotton terylene cloth at −20 to −25° C. The filtercake is rinsed with 2×6 kg methyl tert-butyl ether. The product is dried under vacuum with a maximum oven temperature of 60° C. until it passes drying specifications. Once dry, the product (mesoporphyrin IX formate) is packaged.

Purification of the Mesoporphyrin IX Formate

Excess metal catalyst is removed from the intermediate by charging formic acid with mesoporphyrin IX formate and a quantity of a metal scavenger such as Si-Thiol (approximately 2-10% of the yield of intermediate, based on calculation) with moderate agitation under nitrogen for 16 to 20 hours at 70-80° C. The metal scavenger and excess catalyst is then removed by reducing the temperature to 20-25° C., and then charging a filtering aid such as celite (~5%/0.3 kg) and additional formic acid (~32 kg) into the mixture. The mixture is then filtered and vacuum distilled. The concentrated filtrate is slowly added to a mixture of purified water (52 kg) and 31% hydrochloric acid (9.3 kg) (by calculation based on the quantity of dry intermediate). Gentle agitation and a temperature of 20-25° C. is maintained for a period of 2-3 hours. The resultant mesoporphyrin IX dihydrochloride in suspension is isolated by filtration and dried on the filter while passing a stream of nitrogen through the filter.

The procedure described immediately above may be repeated at least one or two more times for a total of at least 1-3 purifications. Adequate results have been obtained with one purification step.

Step 2

An inerted 200 liter reaction vessel is charged with approximately 2.8 kg of mesoporphyrin IX dihydrochloride, 3.3 kg tin chloride and 73 kilogram acetic acid. The suspension is moderately agitated at 20-25° C., for a minimum of 30 minutes. The suspension is vigorously agitated for a minimum of 30 minutes at a temperature of 20-25° C., while bubbling in a mixture of 6% oxygen in nitrogen. With vigorous agitation under nitrogen and maintaining a 6% oxygen in nitrogen purge, the reaction mixture is heated to reflux (ca 115° C.) and maintained for 24 to 26 hours.

The 6% oxygen in nitrogen purge is shut off. The reaction is cooled to 60-70° C. and approximately 28 kg of purified (de-ionized) water is added over a minimum of 30 minutes. With moderate agitation, the reaction temperature is cooled to 20-25° C. over a minimum of 30 minutes. The reaction mixture is agitated at 20-25° C. for a minimum of 1 hour. The product is filtered through a cotton terylene cloth and the filtercake rinsed with 11 kg purified water. The wet filtercake is transferred to a 200 L reaction vessel followed by 40 kg purified water, 6.6 kg 31% hydrochloric acid. The transfer lines are rinsed with 10 kg purified water. With moderate agitation, the suspension is warmed to 85-95° C. for a period of 1-2 hours. The reaction mixture is cooled to 20-25° C. The suspension is agitated at 20-25° C. for a minimum of 30 minutes. The product is filtered through a cotton terylene cloth and the filtercake rinsed with 11 kg purified water. The product is dried under a stream of nitrogen on the filter until it passes drying specifications. Once dry, the crude product (substantially pure (about or more than 95%) tin (IV) mesoporphyrin IX dichloride) is packaged. Typically, the crude, substantially pure tin mesoporphyrin dichloride product is isolated with a yield of 2.2 kg and 97% purity.

Step 3

An inerted 100 L reactor without agitation is charged with approx. 2.2 kg crude, substantially pure tin mesoporphyrin dichloride, formed via Steps 1 and 2; 0.3 kg hyflo supercel, 0.1 Kg DARCO KB, and 19 kg WFI (water for injection). With moderate agitation at the reactor is charged with 1.5 kg 28% ammonium hydroxide. The resultant solution is agitated at 20-25° C. for 1 to 2 hours, prior to testing pH to ensure that it is equal to or greater than 9. If not, additional ammonium hydroxide is added in small portions until this pH level is achieved. With moderate agitation, the suspension is agitated at 20-25° C. for a minimum of 1-2 hours. The suspension is filtered through a filter to remove solids, leaving a filtrate. The filter cake is rinsed with 7 kg WFI. An inerted 200 L reactor is charged with 58 kg acetic acid and 2.4 kg 31% hydrochloric acid. With moderate agitation, under nitrogen while maintaining a temperature of 20-25° C. the filtrate is added to the acetic acid/HCl solution over a minimum of 45 minutes. The resultant suspension is agitated for a minimum of 15 minutes at 20-25° C. prior to testing the pH level to ensure that the final pH is about less than or equal to 1. If not, additional hydrochloric acid is added in small portions until this pH level is achieved. The suspension is then agitated at 20-25 C for 1-2 hours. The product is filtered through a cotton terylene cloth and the filter cake is rinsed with 10 kg WFI.

The procedure described immediately above may be repeated at least one or two more times for a total of at least 1-3 purifications. Adequate results have been obtained with one purification step.

Without agitation, the wet filter cake and 26 kg WFI are transferred into a 200 L reactor. With moderate agitation, under nitrogen at 20-25° C., 15.5 kg of 31% HCl and 5 kg WFI are charged into the reactor. The mixture is heated to 85-90° C. and agitated for 16-18 hours. While moderately agitating the vessel contents, the temperature of the mixture is lowered to 20-25° C. and the agitation is continued for at least one hour. The reaction mixture is then filtered. The filter cake is rinsed with a mixture of 19 kg WFI and 0.7 kg 31% HCl.

The filter cake product is dried by passing a stream of nitrogen through the filter and applying heat to the filter apparatus until it passes drying specifications. Once dry, the product (tin (IV) mesoporphyrin IX dichloride or stannsoporfin) is packaged and is of pharmaceutical grade quality and purity, as verified by analytical HPLC technique. Typically, the final product is isolated with a yield of 1.2 kg with a purity exceeding 97%).

While foregoing is directed to the preferred embodiment of the present invention, other and further embodiments of the invention may be devised without departing from the basic scope thereof, and the scope thereof is determined by the claims that follow.

What is claimed is:

1. A process of preparing mesoporphyrin IX formate comprising the steps of:
    (a) subjecting a mixture of hemin and a hydrogenation catalyst in formic acid to hydrogen at a temperature of 85-95° C. and
    (b) followed by subsequently subjecting said mixture to hydrogen at a temperature of from 45-50° C., to produce mesoporphyrin IX formate, having the following formula:

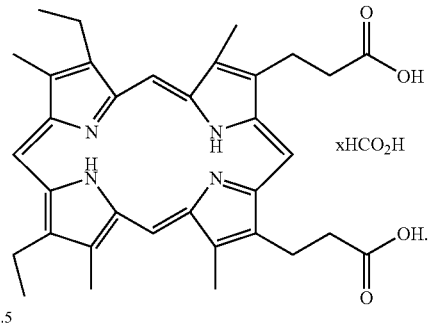

$x = 0.5 - 2.5$

2. The process of claim 1, wherein the hydrogen of step (a) is at a pressure of about 30-60 psi.

3. The process of claim 1, wherein the hydrogen of step (b) is at a pressure of 30-60 psi.

4. The process of claim 1, wherein step (a) endures for about 1-3 hours.

5. The process of claim 4, wherein step (a) endures for about 1 hour.

6. The process of claim 1, wherein the hydrogen of step (a) is at a temperature of about 90° C.

7. The process of claim 1, wherein step (b) endures for about 3-6 hours.

8. The process of claim 1, wherein said hydrogenation catalyst is selected from the group consisting of: palladium, platinum, nickel, and palladium on carbon.

9. The process of claim 1, further comprising minimizing the exposure of the reaction to visible or ultraviolet light.

10. The process of claim 1, further comprising:
    (c) recovering the mesoporphyrin IX formate.

11. The process of claim 10, wherein said recovering is by the addition of ethers.

12. The process of claim 1, further comprising:
    (c) dissolving the formate in formic acid and using a metal scavenger to purify the formate by removing residual metal catalysts.

13. The process of claim 12, wherein said metal scavenger is selected from the group consisting of: Si-thiol, Si-thiourea, Si-triamine, and Si-triaminetetraacetatic acid.

14. The process of claim 11, wherein the ether is selected from the group consisting of: methyl tert-butyl ether, diethyl ether, and di-isopropyl ether.

* * * * *